United States Patent [19]

King

[11] 4,401,834
[45] Aug. 30, 1983

[54] PROCESS FOR PRODUCING ALCOHOLS

[75] Inventor: Terry S. King, Baton Rouge, La.

[73] Assignee: Exxon Research & Engineering Co., Florham Park, N.J.

[21] Appl. No.: 383,458

[22] Filed: Jun. 1, 1982

[51] Int. Cl.³ .................... C07C 29/14; C07C 29/16; C07C 29/88

[52] U.S. Cl. .................. 568/881; 568/492; 568/882; 568/883; 568/914

[58] Field of Search ............... 568/881, 882, 883, 492, 568/914

[56] References Cited

U.S. PATENT DOCUMENTS

| | | | |
|---|---|---|---|
| 2,595,096 | 4/1952 | Parker | 260/638 |
| 2,638,487 | 5/1953 | Russum et al. | 568/882 |
| 2,751,403 | 6/1956 | Mertzweiller | 260/414 |
| 2,757,203 | 7/1956 | Hale | 260/604 |
| 2,760,994 | 8/1956 | Gwynn | 568/881 |
| 2,771,493 | 11/1956 | Jacks et al. | 568/881 |
| 2,779,794 | 1/1957 | Catterall | 260/604 |
| 2,809,220 | 10/1957 | Mertzweiller | 260/638 |
| 2,905,716 | 9/1959 | Buchner et al. | 260/601 |
| 3,014,970 | 12/1961 | Johnson et al. | 560/882 |
| 3,092,670 | 6/1963 | Gwynn et al. | 260/638 |
| 3,102,150 | 8/1963 | Hunter et al. | 568/881 |
| 3,127,451 | 3/1964 | Berkeley et al. | 568/882 |
| 3,255,259 | 6/1966 | Mertzweiller et al. | 568/881 |
| 3,301,909 | 1/1967 | Kawasaka et al. | 568/881 |
| 3,819,728 | 6/1974 | Kwantes et al. | 568/914 |
| 4,255,279 | 3/1981 | Spohn et al. | 252/413 |

FOREIGN PATENT DOCUMENTS

| 715390 | 9/1954 | United Kingdom | 2/3 |
| 1219038 | 1/1971 | United Kingdom | 568/881 |

*Primary Examiner*—J. E. Evans
*Attorney, Agent, or Firm*—Jack B. Murray, Jr.

[57] ABSTRACT

An improved process for producing alcohols which comprises passing a demetalled hydroformylation liquid effluent comprising aldehyde and alcohol and containing acetal impurities to a thermal treatment zone; subjecting the demetalled hydroformylation effluent in the thermal treatment zone in the absence of added acidic compounds and in the presence of water to a temperature of from about 350° to 500° F. for a time sufficient to convert at least a major portion of the acetal impurities to the corresponding aldehydes and alcohols and to form an aldehyde-containing liquid containing substantially reduced levels of the acetal impurities; withdrawing the aldehyde-containing liquid from the thermal treatment zone and rapidly cooling the liquid to a temperature of about 300° F. or below; and passing the cooled liquid to a hydrogenation zone for hydrogenation in the presence of a hydrogenation catalyst and gaseous hydrogen of at least a portion of the aldehydes to the corresponding alcohols at a temperature of from about 150° to 350° F.

9 Claims, 4 Drawing Figures

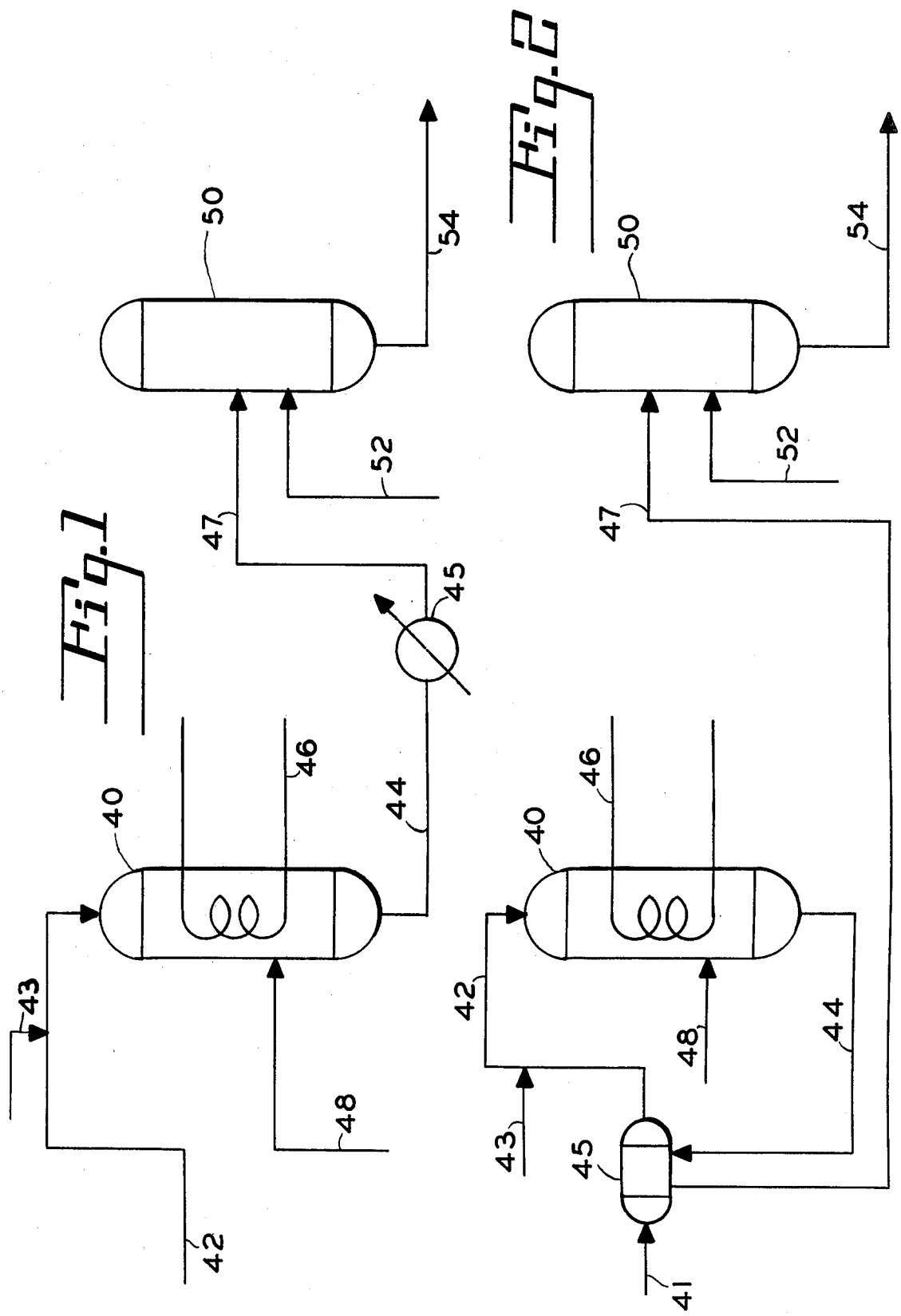

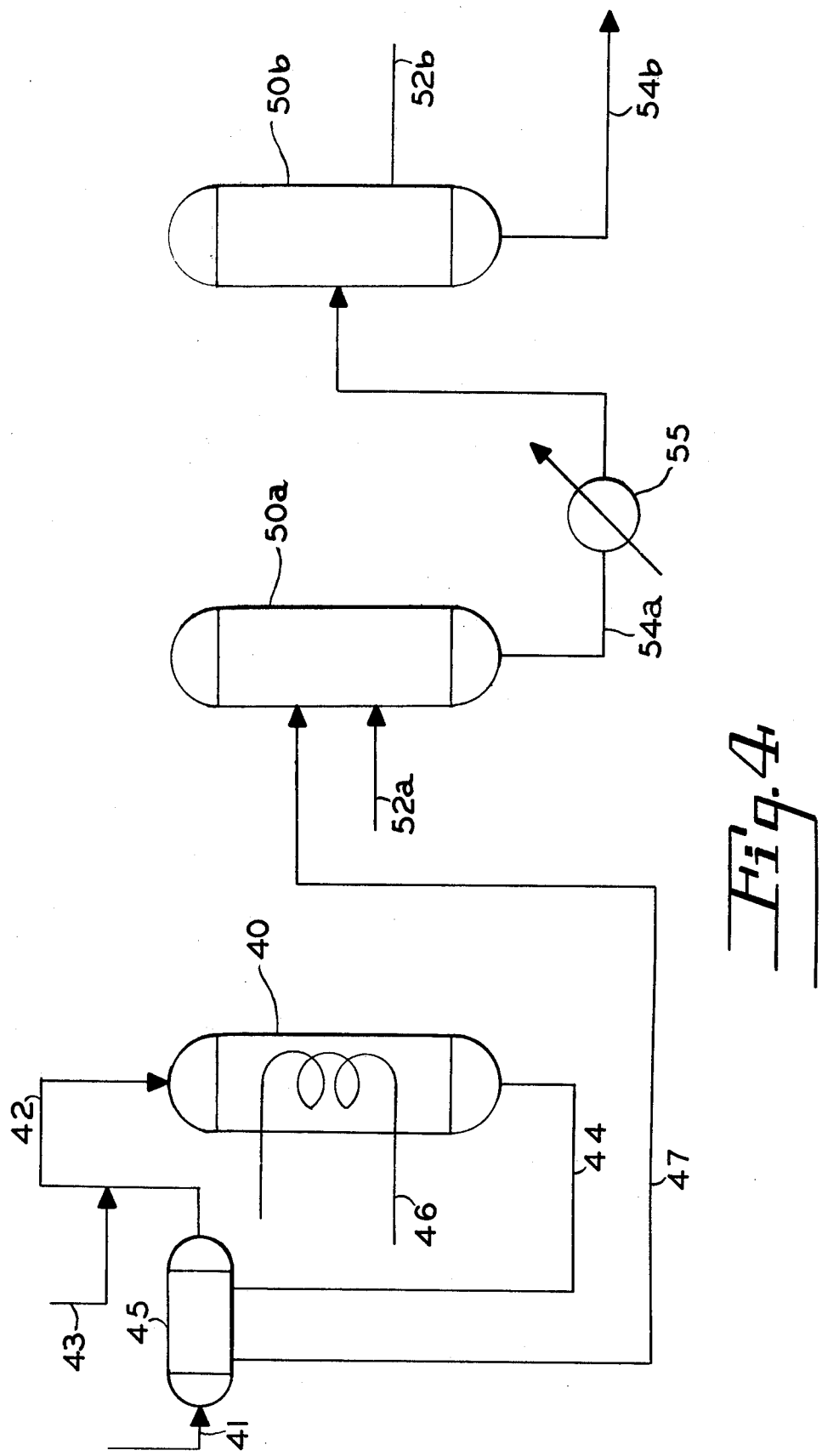

PROCESS FOR PRODUCING ALCOHOLS

BACKGROUND OF THE INVENTION

1. Field of the Invention

This invention relates to the production of alcohols and more specifically to an improved process for producing alcohols by hydrogenation of aldehydes which have been prepared by an oxo reaction.

2. Description of the Prior Art

The oxo process for preparing oxo alcohols is well kown and in general involves three major stages. In the first stage, hydrogen and carbon monoxide are reacted with an olefin in the presence of a hydroformylation catalyst at elevated temperature and pressure to obtain a hydroformylation reaction effluent containing an aldehyde product having one more carbon than the feed olefin. In the second stage, the hydroformylation reaction effluent is then treated to remove the metal hydroformylation catalyst such as by heating the hydroformylation effluent to convert dissolved cobalt carbonyl catalyst into a form which is insoluble in the liquid effluent, followed by separation of the solids (e.g., by direct deposition on inert packings contained in the thermal demetalling vessel, filtration and other means). In the third stage, the demetalled hydroformylation is subjected to hydrogenation conditions. These hydrogenations generally employ one of two classes of catalysts: (1) high temperature catalysts, such as metallic nickel or cobalt, and sulfactive catalysts such as the sulfides of tungsten, molybdenum and nickel, which are employed at temperatures of from about 275° to 500° F., and (2) low temperature catalysts such as copper chromite (mixture of Cr and Cu oxides) which are used at temperatures of from about 150° to 300° F.

Illustrative of prior art methods for demetalling the hydroformylation reaction mixture is U.S. Pat. No. 2,779,794, in which the effluent from the hydroformylation is heated at a temperature of 250° to 350° F. and a pressure of 100 to 200 psi to convert dissolved cobalt carbonyl into a form which is insoluble in the product aldehyde. The cobalt solids are then removed by settling and the demetalled aldehyde layer is cooled and ultimately passed to hydrogenation. Thermal demetalling methods are also discussed in U.S. Pat. Nos. 2,757,203 (300°–400° F.); 2,809,220 (150°–500° F.); and 2,905,716 (302°–392° F.).

Acetals are formed as by-products during the above process and constitute a yield loss to the desired oxo alcohols. Several methods have been developed to minimize this source of yield loss. In U.S. Pat. No. 2,595,096, the demetalled oxo reactor effluent, which has been demetalled at a temperature of from 200° to 450° F., is subjected to hydrogenation to form a hydrogenation effluent which contains the desired oxo alcohol, unconverted aldehyde, lights, inerts and a substantial portion, up to 50 volume %, acetals.

This stream is subjected to several distillative steps to remove inerts, lights and the alcohol product. The resulting acetal-containing stream is then hydrolyzed (using either dilute mineral acid at 200° to 250° F., or steam at 300° to 400° F.) to liberate additional alcohols and aldehydes for recovery and recycle to the feed line to the hydrogenation reactor.

The process of U.S. Pat. No. 2,757,203 subjects the hydroformylation effluent to a steam distillation in the presence of added mineral acid (such as phosphoric acid) to hydrolyze acetal impurities while simultaneously thermally decomposing the cobalt carbonyl catalyst. The overhead vapors from this distillation step comprise aldehydes, water and carbon monoxide gas (the latter being formed from the cobalt catalyst decomposition). These vapors are partially condensed, the gaseous CO is removed and the aqueous and aldehyde layers are separated, with the aldehyde layer being passed to subsequent hydrogenation. In a second embodiment, the patentee hydrogenates a demetalled hydroformylation effluent and treats the hydrogenation effluent by a series of distillations, the first of which is intended to separate aldehydes as overhead using a steam distillation in the presence of added phosphoric acid again to hydrolyze the acetals in the hydrogenation effluent.

U.S. Pat. No. 2,809,220 discloses a process in which water is added to the hydrogenation zone in which a demetalled hydroformylation effluent is subjected to hydrogenation conditions. The patentee indicates that the advantage of water in the hydrogenation zone is to assist in the breakdown of the secondary reaction products, such as acetals, to form additional alcohol product. However, this process employs a high temperature hydrogenation catalyst operating at from 400° to 600° F.

In U.S. Pat. No. 3,092,670, a demetalled hydroformylation effluent is fractionated with steam under controlled conditions to remove as overhead only unreacted olefins. The remainder of the product, including the acetals, is not separated but is passed to the subsequent hydrogenation stage.

U.S. Pat. No. 2,905,716 discloses another method for purification of a hydroformylation reaction effluent containing cobalt catalyst and acetal impurities.

British Patent No. 715,390 performs concurrent decobalting and acetal hydrolysis in the presence of dilute acid or water at temperatures below about 250° F.

SUMMARY OF THE INVENTION

According to the process of this invention, improved yields of oxo alcohols are obtained by subjecting a demetalled hydroformylation liquid effluent in the absence of added acidic compounds to temperatures of at least about 350° F. in the presence of water for a time sufficient to convert at least a major portion of said acetal impurities to the corresponding aldehyde and alcohol and subjecting the thus-treated liquid to hydrogenation conditions in a separate hydrogenation zone for conversion of said aldehydes to said alcohols in the presence of a hydrogenation catalyst and added hydrogen.

It has been surprisingly found that acetal impurities in demetalled hydroformylation effluent can be efficiently converted to the corresponding aldehyde and alcohol by thermal treatment under controlled conditions, without the need for the addition of mineral acids thought to be required by the prior art and without the need to first separate the alcohols and aldehydes from the acetals as required in U.S. Pat. No. 2,595,096. Indeed, it has been surprisingly found that acids, when added to such demetalled hydroformylation effluents, can actually increase rather than decrease the acetal content. There is thus formed by the process of this invention a thermally treated liquid containing substantially reduced quantities of acetal which contains corresponding increased amounts of aldehyde and product alcohol which can then be treated for hydrogenation of the aldehyde to additional alcohol.

BRIEF DESCRIPTION OF THE DRAWINGS

FIG. 1 is a schematic illustration of one embodiment of the process of this invention.

FIG. 2 is a schematic illustration of a second embodiment of this invention employing an effluent/feed heat-exchanger on the feed-side of the thermal treatment vessel.

FIG. 4 is a schematic illustration of yet another embodiment of this invention in which multi-stage hydrogenation is employed.

DETAILED DESCRIPTION OF THE INVENTION

Figure 3:
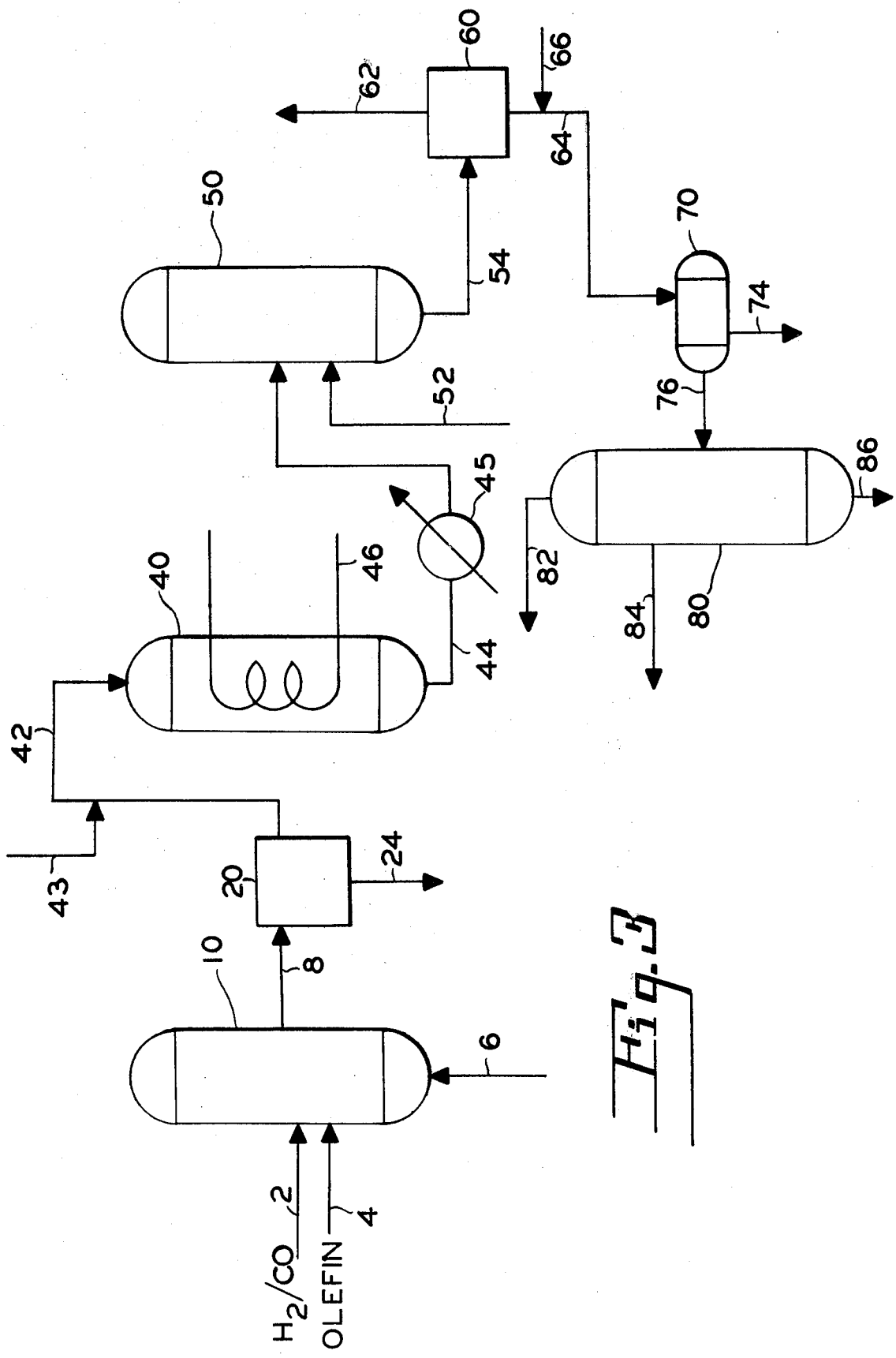
FIG. 3 is a schematic illustration of the process of this invention integrated with a hydroformylation process.

Referring to FIG. 1, a demetalled hydroformylation effluent containing acetal impurities is passed via conduit 42 to thermal treatment zone 40 wherein the liquid is heated to a temperature of at least about 350° F., e.g., by means of steam coils 46, a reboiler (not shown) or other means, to convert at least a major portion of the acetal impurities to the corresponding aldehydes and alcohols. The liquid feed in conduit 42 will be substantially free of metal hydroformylation catalyst. In the case of cobalt carbonyl catalyst, this demetalled liquid will generally contain less than about 10 ppm by weight of cobalt catalyst, calculated as elemental cobalt. In addition, the demetalled hydroformylation liquid effluent will comprise oxo aldehydes in addition to some oxo alcohols, unreacted olfins, paraffins, acetals and other heavy byproducts. While the precise composition of the demetalled hydroformylation liquid effluent is not critical to the process of this invention and can vary widely (depending on such factors as the olefin selected for hydroformylation, the conditions of hydroformylation and other factors), this liquid feed to thermal treatment zone 40 will generally comprise from about 5 to 50 wt.% oxo aldehyde, from about 5 to 50 wt.% oxo alcohol, from about 5 to 50 wt.% acetal, 5 to 30 wt.% unreacted olefins and paraffins and 2 to 20 wt.% other heavy by-products (materials other than the acetal boiling higher than the other, above components).

In thermal treatment zone 40, the liquid feed is heated to, and maintained at, a temperature of at least about 350° F., preferably from about 350° to 500° F., more preferably from about 400° to 475° F., and most preferably from about 420° to 450° F. The pressure in zone 40 can vary widely and is not critical. Therefore, atmospheric, subatmospheric or superatmospheric pressures can be employed, with pressures of from about 50 to 1000 psig being typically employed. The liquid introduced via conduit 42 should be maintained at the selected temperature in thermal treatment zone 40 for a time of from about 5 to 120 minutes, preferably from about 5 to about 30 minutes.

Gaseous hydrogen can be optionally introduced into thermal treatment zone 40 by means of conduit 48 in order to minimize the extent to which dehydrogenation reactions might otherwise occur, such dehydrogenation reactions being illustrated by carbonaceous deposite on internal metal surfaces of process equipment. The amount of such $H_2$ can vary widely, and, where employed, $H_2$ partial pressure in zone 40 will generally range from about 50 to 1000 psig, although higher or lower pressures can also be used.

The liquid in thermal treatment zone 40 should also contain water, which can be added as required to the liquid feed via conduit 43, or introduced directly into zone 40 (as liquid water or steam) via a separate conduit (not shown). Water, when added in the following amounts, avoids the formation of high-boiling by-products which can result from the degradation of the acetals in the absence of sufficient water. The water should be added in an amount at least sufficient to provide the moles of water stoichiometrically required to react with the quantity of acetal in the liquid feed. The amount of water introduced to zone 40 will generally range from about 1 to 10 mols, and preferably from about 2 to 5 mols of water, per mol of acetal in the demetalled liquid introduced thereto.

Conventional equipment such as an insulated holding drum and the like can be employed to house thermal treatment zone 40, which can also be provided with suitable stirring devices such as impellers, gas spargers and the like. The preferred apparatus for this service is an insulated, baffled drum that will operate in a plug flow mode.

In zone 40, the acetal impurities are hydrolyzed to the corresponding aldehydes and alcohols. By way of illustration, the hydrolysis of the didecylacetal of decylaldehyde can be represented by the equation (I):

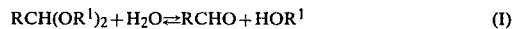

$$RCH(OR^1)_2 + H_2O \rightleftharpoons RCHO + HOR^1 \qquad (I)$$

wherein R is $CH_3(CH_2)_9-$ and $R^1$ is $-(CH_2)_9CH_3$. When the demetalled hydroformylation liquid contains a mixture of different acetals, of course, a mixture of different alcohols and aldehydes will result by hydrolysis of the corresponding acetals.

It has been surprisingly found that acetals in these demetalled hydroformylation liquids undergo a rapid and efficient conversion under the above conditions to the aldehydes and alcohols in the absence of added acidic compounds, and that it is not necessary to add a dilute mineral acid or other acidic moieties to the liquid to catalyze the hydrolysis in order to achieve prehydrolysis at commercially significant rates. This invention, therefore, avoids the use of expensive corrosive-resistant treatment vessels for zone 40 and downstream conduits and avoids the need to caustic treat and/or carefully monitor an acid-tested liquid in order to prevent excess acid from passing into process equipment which is not constructed of corrosion-resistant materials.

There is thus formed a liquid which can be withdrawn from zone 40 and which contains substantially reduced quantities of acetals, the acetal concentrations in this liquid being generally reduced across zone 40 to a level of less than about 3 wt.%, preferably less than about 2 wt.%, acetal.

The liquid effluent withdrawn from zone 40 via conduit 44 is then cooled to a temperature of about 275° F. or below, and preferably to a temperature of from about 150° to 250° F., for example by means of heat exchanger 45. The liquid is preferably rapidly cooled to the selected temperature, with a liquid residence time in heat exchanger 45 of less than about 5 minutes, preferably from about 1 to 3 minutes, in order to avoid the formation of substantial additional quantities of acetal prior to hydrogenation. The cooled liquid is then passed to conduit 47 and introduced into hydrogenation zone 50 wherein the liquid is hydrogenated in the presence of a hydrogenation catalyst and gaseous hydrogen. Gaseous hydrogen can be introduced to zone 50 via conduit 52. The amount of hydrogen which is thereby introduced can vary widely depending on such factors as the particular aldehyde to be hydrogenated, the amount of hydrogen passing to zone 50 via conduit 47 (as a result of the injection of hydrogen via conduit 48 into the earlier thermal treatment step) and other factors. Generally, however, hydrogen will be introduced to hydrogenation zone 50 in an amount sufficient to provide a hydrogen partial pressure therein of from about 500 to 3500 psig, preferably from about 500 to 1200 psig. If desired, gaseous hydrogen can also be introduced directly into the cooled liquid in conduit 47 (e.g., by means of a separate hydrogen injection conduit, not shown) in order to pre-mix the hydrogen with this liquid and/or for further temperature control of the cooled liquid using an available, cooled hydrogen gas stream.

The hydrogenation is conducted at a temperature within the range of from about 150° to 350° F., preferably from about 200° to 300° F., employing as a hydrogenation catalyst any conventional hydrogenation catalyst which is active for hydrogenation of the aldehydes passed to zone 50 at the foregoing, selected temperatures. For example, the hydrogenation catalyst can comprise one or more members selected from the group consisting of copper, nickel, cobalt and ruthenium catalysts, including alloys and mixtures of the foregoing, either supported or unsupported on inert supports (such as alumina, silica and the like). The catalyst can also contain any of the conventional hydrogenation promoters such as the alkali and alkaline earth metals. Illustrative catalysts include copper chromite, metallic nickel, metallic cobalt, metallic ruthenium, nickel-chromium alloys, nickel-copper-cobalt alloys, metallic copper and the like. Preferred hydrogenation catalysts are copper chromite, metallic Ni, and nickel-chromium alloys.

The liquid hourly space velocity in hydrogenation zone 50 will generally be from about 0.2 to 5 v/v/hr., and preferably from about 0.5 to 2 v/v/hr.

The hydrogenation reaction occurring in zone 50 is exothermic and temperature control within zone 50 can be effected by means of controlling the temperature of the liquid feed introduced via conduit 47, cooling the hydrogen feed introduced via conduit 52 or other means.

If desired, water can be introduced into hydrogenation zone 50, generally in an amount of from about 1 to 8 vol.%, based on the volumetric flow of the feed in conduit 47 in order to reduce by-product formation. To the extent that the desired amount of water is not contained in the aldehyde feed in conduit 47, a separate water injection conduit (not shown) to zone 50 can be provided.

FIG. 2 illustrates a preferred embodiment in which the demetalled feed to zone 40 is first passed via conduit 41 to heat exchanger 45 to pre-heat the demetalled liquid to a temperature of from about 300° to 400° F. by indirect heat exchange with the liquid effluent from zone 40, which is passed thereto via conduit 44. Additional cooling of the withdrawn liquid in conduit 47 can then be provided as required by a further subsequent indirect heat exchanger (not shown) to which a cooling medium, such as cooled water, is supplied. In combination, the heat exchanger 45 and any subsequent further cooler provide the rapid cooling described above with respect to FIG. 1 to minimize the extent to which acetals are reformed prior to distillation column 50. It will be understood that the cooling to be achieved by heat exchanger 45 in the embodiment of FIG. 2, and in any subsequent further cooler (not shown), will result in the above-discussed rapid cooling of the liquid effluent withdrawn via conduit 44 from treatment zone 40 in order to achieve a total residence time in these exchangers of less than about 5 minutes.

Referring now to FIG. 3, there is illustrated a process of this invention integrated with oxo reactor 10, demetalling zone 20 and a method for recovering the oxo alcohol product withdrawn via conduit 54 from the hydrogenation zone 50.

An olefin feed is introduced via conduit 2 to oxo reactor 10 to which is also fed a mixture of CO and $H_2$ (synthesis gas) via conduit 4 and an organic liquid containing dissolved cobalt catalyst via conduit 6. The oxo reaction is conventional and typically employs a temperature of from about 150° to 460° F. and syn gas pressures of from about 1500 to 4500 psig.

The olefin fed to the oxo reactor 10 can comprise any carbon compound containing olefinic linkages. Thus, straight and branch-chained olefins and diolefins such as propylene, butylene, pentene, hexene, heptene, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired.

Also suitable are olefins bearing functional groups such as $-C\equiv N$, $-OH$, -halide and the like which do not adversely affect the hydroformylation reaction. Illustrative of such functionally substituted olefins are acrylonitrile, allyl alcohol, alkenyl esters of acrylic acid, acrylic acid, vinyl halides and the like. Preferred are olefins having from 2 to 20 carbon atoms (such as ethylene, propylene, butenes, pentenes, hexenes, heptenes, octenes, decenes, dodecenes and the like) and aryl-substituted alpha-olefins (such as styrene, stilbene, divinylbenzenes and the like).

Crude oxo product, comprising dissolved cobalt catalyst, unreacted olefin, hydroformylation product and hydroformylation by-products, is withdrawn from oxo reactor 10 via conduit 8 and passed to demetalling zone 20 wherein the stream can be treated by any convenient means to remove and/or recover the cobalt values therefrom. Illustrative, but not limiting, of the demetalling processes which have been developed are those disclosed in U.S. Pat. Nos. 2,751,403 and 4,255,279, and in co-pending applications Ser. No. 333,693, filed Dec. 23, 1981, Ser. No. 333,734, filed Dec. 23, 1981, and Ser. No. 337,593, filed Jan. 7, 1982, the disclosures in each of which are hereby incorporated by reference.

From demetalling zone 20 the cobalt values are withdrawn via conduit 24 and a demetalled oxo effluent containing oxo aldehydes, some alcohols, in addition to acetal impurities and substantially free of cobalt values (generally containing less than about 10 ppm of cobalt catalyst, calculated as elemental Co), is withdrawn via conduit 42 and passed to zones 40 and 50 for treatment as described above.

The effluent withdrawn from hydrogenation zone 50 via conduit 54 can then be degassed into zone 60, employing conventional equipment and methods to remove excess hydrogen and other gasses (via conduit 62). The resulting crude hydrogenation effluent can be then contacted with an alkaline reacting agent, such as caustic, which can be introduced to the liquid in conduit 64 via conduit 66, in order to neutralize any acidic by-products remaining in the thus-contacted liquid, e.g., by-products formed during hydrogenation. The resulting mixture is passed to liquid/liquid phase separator 70 for separation of the organic and aqueous layers. The aqueous layer is withdrawn via conduit 74 and the organic layer containing the oxo alcohol product can then be passed to product recovery zone 80 for separation and recovery via conduit 82 of a first stream comprising light materials, such as reaction by-products and impurities (largely olefins and paraffins), and to form a product stream containing the desired oxo alcohols, which can be withdrawn via conduit 84. A heavies-containing stream can be withdrawn via conduit 86.

Especially preferred as demetalled hydroformylation effluent for thermal treatment in accordance to the process of this invention for the reduction of acetal impurity content are hydroformylation effluents containing straight and branch-chained saturated aliphatic aldehydes having from 6 to 20 carbon atoms, which have been formed by hydroformylation of an olefin having one less carbon atom per molecule.

Exemplary of such aldehydes, therefore, are caproaldehyde, heptaldehyde, octaldehyde, decaldehyde, dodecaldehyde and $CH_3(CH_2)_{14}CHO$. Accordingly, the alcohols which will be produced will correspond to the aldehyde and will therefore generally comprise (straight and branched chain) saturated aliphatic alcohols having from 6 to 18 carbon atoms per molecule. Exemplary product alcohols are primary normal aliphatic alcohols such as 1-hexanol, 1-heptanol, 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol, and the like, primary branched aliphatic alcohols such as 2-methyl-1-pentanol, 2-ethyl-1-butanol, 2-ethyl-1-hexanol, 3,5-dimethyl-1-hexanol, 2,2,4-trimethyl-1-pentanol, and the like, secondary aliphatic alcohols such as 4-methyl-2-pentanol, 2-octanol, 2,6-dimethyl-4-heptanol, 2,6,8-trimethyl-4-nonanol, and the like, and highly branched detergent alcohols such as tridecyl alcohol, hexadecyl alcohol, tetradecyl alcohol, heptadecyl alcohol and the like. It will be understood that alcohol mixtures can also be formed. Thus, for example hexylalcohol will generally be a mixture of 1-hexanol, methyl-1-pentanols and 2-ethyl-1-butanol. Similarly, isooctyl alcohol is generally a mixture of 3,4-dimethyl-1-hexanol, 3,5 dimethyl 1-hexanol, 4,5 dimethyl-1-hexanol, methyl-1-heptanols, and other primary alcohols.

Most preferably, the demetalled hydroformylation effluent contains such aldehydes having from 7 to 13 carbon atoms per molecule, and the preferred, corresponding oxo alcohols are therefore alcohol containing from 7 to 13 carbon atoms per molecule and having the corresponding carbon structure.

It will be apparent from the foregoing that the hydrogenation effected in zone 50 can be performed using a plurality of hydrogenation vessels, either in series or in parallel. In order to ensure the minimum formation of acetal impurities following a first such hydrogenation zone, it is preferred to employ interstage cooling, as by means of a suitable heat exchanger, in order to rapidly cool the partially hydrogenated effluent before passing this effluent as feed to a subsequent hydrogenation zone. Referring to FIG. 4, such an embodiment is illustrated wherein the liquid withdrawn from thermal treatment zone 40 is passed via conduits 44 and 47 to first hydrogenation zone 50a for hydrogenation in the presence of gaseous hydrogen, at least part of which can be introduced via conduit 52a as described above. The liquid effluent from this first hydrogenation zone is withdrawn via conduit 54a and rapidly cooled to a temperature of from about 150° to 300° F., such as by use of an in-line heat exchanger 55, to provide a cooled, partially hydrogenated effluent which is then introduced as feed to second hydrogenation zone 50b. In the second hydrogenation zone, additional quantities of aldehyde in the partially hydrogenated feed thereto are subjected again to hydrogenation conditions such as have been described earlier for zone 50, in the presence of added hydrogen gas, introduced by via conduit 52b. The more fully hydrogenated effluent from second hydrogenation zone 50b is withdrawn via conduit 54b and can be passed to products recovery steps, as described above.

The process of this invention can be further illustrated by reference to the following examples, wherein parts are by weight unless otherwise indicated.

EXAMPLE 1

To illustrate the non-catalytic process of this invention for minimizing alcohol yield losses due to acetal impurities, a series of tests were performed in which a 4000 cc carbon steel reactor was charged with 3000 cc of a demetalled hydroformylation effluent comprising 8 wt.% water, 14 wt.% unconverted $C_9$ olefin, 24 wt.% decyl aldehyde, 28 wt.% decyl alcohol, 7 wt.% heavy materials (materials other than the acetal boiling higher than the above components), and 27 wt.% didecyl acetal of decyl aldehyde. The liquid thus charged to the reactor was also characterized by a carbonyl number of about 120 milligrams KOH/gm. of sample. The reactor was then pressured to 3000 psig with gaseous hydrogen and the contents were then heated according to a predetermined temperature schedule. The acetal weight percent in the liquid phase, found by gas chromatographic analysis of liquid aliquots periodically withdrawn from the reactor by means of a capillary sampling tube, was followed as a function of time and temperature. The data thereby obtained are set forth in Table I below.

TABLE I

| Sample No. | Time (hr.) | Temp. (°F.) | Acetal Content (wt. %) | Overall Acetal Conversion (wt. %) |
|---|---|---|---|---|
| 1 | 0.5 | 200 | 27 | 0 |
| 2 | 1.0 | 200 | 27 | 0 |
| 3 | 1.5 | 200 | 27 | 0 |
| 4 | 2.25 | 300 | 26 | 4 |
| 5 | 2.5 | 300 | 25 | 7 |
| 6 | 3.0 | 300 | 24 | 11 |
| 7 | 3.5 | 300 | 18 | 33 |
| 8 | 4.0 | 300 | 12 | 56 |
| 9 | 4.25 | 300 | 3 | 89 |
| 10 | 4.5 | 400 | 1.5 | 94 |
| 11 | 4.75 | 400 | 1.5 | 94 |
| 12 | 5.25 | 400 | 1.5 | 94 |
| 13 | 5.5 | 500 | 0.5 | 98 |
| 14 | 5.75 | 500 | 0.5 | 98 |

EXAMPLE 2

Following the procedure of Example 1, a separate series of runs were made in which the acetal conversion was followed as a function of time as isothermal conditions, for select temperatures. The data thereby obtained are set forth in Table II below.

TABLE II

| Sample No. | Temp. (°F.) | Time (hrs.) | Overall Acetal Conversion (wt. %) |
|---|---|---|---|
| 1 | 300 | 1.0 | 15 |
| 2 | 300 | 2.0 | 42 |
| 3 | 300 | 3.0 | 62 |
| 4 | 300 | 4.0 | 74 |
| 5 | 300 | 7.0 | 88 |
| 6 | 300 | 24.0 | 86 |
| 7 | 350 | 0.25 | 44 |
| 8 | 350 | 0.50 | 80 |
| 9 | 350 | 0.75 | 89 |
| 10 | 350 | 1.0 | 90 |
| 11 | 350 | 1.25 | 91 |
| 12 | 350 | 8.0 | 92 |
| 13 | 400 | 0.25 | 94 |
| 14 | 400 | 0.50 | 94 |
| 15 | 400 | 0.75 | 94 |
| 16 | 485 | 0.25 | 98 |
| 17 | 485 | 0.50 | 98 |
| 18 | 485 | 0.75 | 98 |

EXAMPLE 3

A demetalled hydroformylation effluent comprising 11 wt.% unconverted $C_9$ olefin and paraffins, 23 wt.% decyl aldehyde, 32 wt.% decyl alcohol, 7 wt.% of heavy materials (materials, other than the acetal, boiling higher than the above components), and 27 wt.% didecyl acetal of decyl aldehyde was passed to a thermal treatment vessel, comprising a 55 cc carbon steel reactor which is maintained at 450° F. by means of a heated, fluidized sand bath. The liquid feed rate was such as to maintain a liquid residence time of about 0.3 hours. Gaseous hydrogen was introduced at a rate of 10 standard liters per hour to provide a pressure of 1050 psig in the thermal treatment vessel. In addition, water was introduced with the organic feed in an amount of 4.2 volume percent of the feed.

The thermally treated effluent from this first vessel was then passed to a hydrogenation reactor, comprising a second, 75 cc carbon steel reactor, which contained 50 cc of copper chromite hydrogenation catalyst (G-22 Girdler catalyst, manufactured by United Catalyst Industries) and comprising 31 wt.% Cu, 25 wt.% Cr and 10 wt.% Ba (calculated as the metals) which was pre-reduced in the reactor, before passing liquid feed thereto, by heating in the presence of gaseous $H_2$ (1000 psi) at 750° F. for 4 hours. Gaseous hydrogen was introduced by means of a separate line at a rate of 130 standard liters per hour to provide a partial pressure of hydrogen of 1050 psig. The second reactor was also heated by means of a heated fluidized sand bath to a temperature of 250° F., and a liquid residence time in the reactor of 0.35 hours was maintained.

The feed to the second reactor was cooled to 70° F. by means of a cold water cooling coil.

The feed to the thermal treatment vessel and the effluent from the second reactor were analyzed by gas chromatography, and the resulting data are set forth in Table III below.

TABLE III

| G.C. Analysis (wt. %) | Liquid Feed to Thermal Treatment Vessel | Liquid Feed[4] to Hydrogenator | Liquid Effluent From Hydrogenator |
|---|---|---|---|
| Lights[1] | 11.3 | 11.3 | 11.4 |
| Decyl Aldehyde | 23.4 | 31.5 | 15.2 |
| Decyl Alcohol | 31.8 | 48.1 | 64.7 |
| $C_{20}$[2] | 6.7 | 6.7 | 6.3 |
| Acetal[3] | 26.9 | 2.4 | 2.4 |
| Carbonyl No. mg KOH/gm | 110 | 110 | 39 |
| Acid No. mg KOH/gm | 4.8 | N.A. | 3.9 |
| Ester No. mg KOH/gm | 20.4 | N.A. | 16.5 |

[1]organic compounds boiling lower than decyl aldehyde
[2]primarily saturated ethers
[3]didecylacetal of decylaldehyde
[4]determined by calculation, based on a comparative run in which the demetalled hydroformylation effluent was instead passed directly to the hydrogenation reactor (without prior treatment in the thermal treatment vessel) using the above catalyst and hydrogenation conditions; no detectable change in the acetal concentration was observed across the hydrogenation reactor.
N.A. = data not available

EXAMPLE 4

In order to illustrate the unsuitability of acid hydrolysis of the acetals present in the demetalled hydroformylation effluent, a demetalled hydroformylation effluent having the composition set forth in Table IV below (50 milliliters) was contacted with 3 drops of 38 wt.% aqueous HCl solution, which liquid mixture was then stirred at 75° F. and atmospheric pressure. At the end of this time, a liquid sample was then immediately subjected to analysis by gas chromatography, providing the results summarized in Table IV below.

Thus, it was shown that the acid resulted in an increased acetal concentration. Surprisingly, therefore, it was found the acidic hydrolysis of acetals in the environment of demetalled hydroformylation effluents is not required and can be detrimental.

TABLE IV

| G.C. Analysis* (wt. %) | Demetalled Hydroformylation Effluent | Acidified Liquid |
|---|---|---|
| Lights[1] | 19 | 18 |
| Decyl Aldehyde | 49 | 51 |
| Decyl Alcohol | 17 | 14 |
| $C_{20}$[2] | 2.8 | 2.9 |
| Acetal[3] | 11 | 14 |
| Heavies[4] | 0.3 | 0.6 |

[1]organic compounds boiling lower than decyl aldehyde
[2]primarily saturated ethers
[3]didecyl acetal of decyl aldehyde
[4]organic compounds boiling higher than the acetal
*reported on a water-free basis. Liquid feed to hydrogenation was saturated with water (corresponding to a water concentration of about 1 wt. % in the feed).

In the foregoing experiments, acid numbers of the process liquids were determined by mixing 25 ml of isopropyl alcohol with 25 ml of the liquid process sample to which 5 drops of phenolphthalein were added. This mixture was then titrated to a clean end point with 0.5 N KOH. The acid number was then calculated by the expression: $(56.1 \times S \times N) \div W$, wherein S=milliliters of titrant, N=normality of KOH and W=weight of liquid process sample. The ester numbers were determined by adding 25 ml of 0.5 N KOH and 10 ml of isopropyl alcohol to 25 ml of the liquid process sample, followed by refluxing for 30 minutes. The liquid was allowed to cool to room temperature and the reflux condenser was rinsed with 10 ml of isopropyl alcohol.

The resultant liquids were admixed with 250 ml of isopropyl alcohol, and 5 drops of phenolphthalein were added. This liquid was then titrated to a clean end point with 0.5 N HCl (titrant #1). A blank was made by repeating the above steps, but without the liquid process sample (titrant #2). The ester numbers were calculated by the expression:

$$[(56.1 \times (B-A) \times N) \div W] - R,$$

wherein B=cc of titrant #2, A=cc of titrant #1, N=normality of the HCl, W=weight of the liquid process sample, and R=the acid number, determined as above, for the corresponding process liquid. Carbonyl numbers were determined by pipetting 25.0 ml of hydroxylamine hydrochloride reagent into 50 ml of 91 wt.% aqueous isopropanol in a 600 ml beaker, and G grams of liquid sample were then added. (The liquid process sample size, G, was determined by the expression:

$$\log G = 2 - 0.96 \log C.N.$$

wherein C.N.=the carbonyl number of the sample (mg KOH/gm). The resulting liquid mixture was refluxed for thirty minutes under hemispherical condensers and cooled to room temperature, and 25.0 ml of 0.1 N NaOH were then added. The liquid was allowed to stand for 1 hour with occasional stirring, and was then titrated potentiometrically with 0.1 N HCl using a pH of 3.7 as the end point. (If the initial pH was less than 3.7, the above procedure was repeated with a smaller sample size.) The carbonyl number was then determined by the expression:

$$C.N. = [(T-S) \times N' \times 56.1] = [G \times SpG]$$

wherein C.N.=carbonyl number (mg KOH/gm), S=mls of titrant, T=mls of blank titrant (obtained by using the above procedure without adding the liquid process sample), N'=normality of the HCl, G=grams of liquid process sample, and SpG=specific gravity of the liquid process sample, all in consistent units.

It will be obvious that various changes and modifications may be made without departing from the invention and it is intended, therefore, that all matter contained in the foregoing description shall be interpreted as illustrative only and not limitative of the invention.

What is claimed is:

1. An improved process for producing alcohols which comprises:
   (a) passing a demetalled hydroformylation liquid effluent comprising aldehyde and alcohol and containing acetal impurities to a thermal treatment zone;
   (b) subjecting said demetalled hydroformylation effluent in said thermal treatment zone in the absence of added acidic compounds and in the presence of water to a temperature of from about 350° to 500° F. for a time sufficient to convert at least a major portion of said acetal impurities to the corresponding aldehydes and alcohols and to form an aldehyde-containing liquid containing substantially reduced levels of said acetal impurities;
   (c) withdrawing said aldehyde-containing liquid from said thermal treatment zone and rapidly cooling said liquid to a temperature of about 300° F. or below; and
   (d) passing said cooled liquid to a hydrogenation zone for hydrogenation in the presence of a hydrogenation catalyst and gaseous hydrogen of at least a portion of said aldehydes to the corresponding alcohols at a temperature of from about 150° to 350° F.

2. The process of claim 1 wherein gaseous hydrogen is introduced into said thermal treatment zone in an amount sufficient to provide a hydrogen partial pressure therein of from about 50 to 1000 psig.

3. The process according to claim 1 wherein said demetalled hydroformylation liquid effluent contains saturated aliphatic aldehyde having from 6 to 20 carbon atoms, saturated aliphatic alcohol having from 6 to 20 carbon atoms and said acetal impurities.

4. The process according to claim 1 wherein said acetal impurities are contained in said demetalled hydroformylation effluent in an amount of at least about 5 wt.%.

5. The process according to claim 1 wherein said aldehyde-containing liquid withdrawn from said thermal treatment zone contains not greater than about 3 wt.% of said acetal impurities.

6. The process according to claim 1 wherein the hydrogenation catalyst employed in said hydrogenation zone comprises at least one member selected from the group consisting of copper chromite, metallic Ni, metallic Co, metallic Cu, metallic Ru and alloys of any of the foregoing metals.

7. The process according to claim 1 wherein said withdrawn aldehyde-containing liquid is cooled from the temperature employed in said thermal treatment zone to a level of at least about 300° F. or below in a cooling zone in which the liquid residence time is less than about 5 minutes.

8. The process according to claim 1 wherein water is employed in said thermal treatment zone, the water being introduced thereto in an amount of from about 1 to 10 mols of $H_2O$ per mol of acetal introduced to said thermal treatment zone.

9. The process according to claim 1 wherein a partially hydrogenated liquid effluent is withdrawn from said hydrogenation zone at a temperature of from about 300° to 400° F., said withdrawn hydroformylation effluent is rapidly cooled to a temperature of at least about 300° F. and said cooled hydrogenation effluent is passed to a separate hydrogenation zone for hydrogenation of additional quantities of said aldehyde to the corresponding alcohols, said separate, subsequent hydrogenation zone employing a temperature therein of from about 150° to 350° F. and said subsequent separate hydrogenation being effected in the presence of a hydrogenation catalyst and gaseous hydrogen.

* * * * *